United States Patent [19]

Aladjem et al.

[11] 4,097,149

[45] Jun. 27, 1978

[54] QUANTITATIVE PROTEIN ANALYSIS BY IMMUNODIFFUSION

[76] Inventors: Frederick J. Aladjem; Padmasini K. Ayengar, both of Pasadena, Calif.

[21] Appl. No.: 546,351

[22] Filed: Feb. 3, 1975

[51] Int. Cl.² .................................... G01N 27/26
[52] U.S. Cl. ...................... 356/72; 204/180 S; 204/180 G; 204/299 R; 195/103.5 R; 356/201; 356/203
[58] Field of Search ........... 204/180 R, 180 G, 180 S, 204/299; 356/72, 201, 203; 195/103.5 R

[56] References Cited

U.S. PATENT DOCUMENTS

| | | | |
|---|---|---|---|
| 3,096,137 | 7/1963 | Silard | 356/201 X |
| 3,459,948 | 8/1969 | Cosci | 356/203 X |
| 3,553,067 | 1/1971 | Dwyer et al. | 204/180 S |
| 3,924,948 | 12/1975 | Thoden et al. | 356/201 X |

OTHER PUBLICATIONS

Ghanta, et al., "Quan. . . . Immunoelectrophoresis," Chem. Abstracts, vol. 81, 1974, (76181c).
Cawley, "Electrophoresis and Immunoelectrophoresis," Little, Brown and Co., Boston, (1969), pp. 7-21, & 194-199.

Primary Examiner—Arthur C. Prescott

[57] ABSTRACT

Methods are described by which immunochemical procedures such as immunodiffusion and immunoelectrophoresis can be used to provide quantitative measurement of the concentration of individual proteins in fluids such as serum, spinal fluid, tissue extracts and the like. That is accomplished typically by making quantitative optical measurements of the zones of precipitation which are produced, in parallel with those of standard preparations containing known concentrations of the proteins to be determined; deriving from the measurements of the precipitation zones selected parameters; and comparing the selected values of the experimental and reference preparations. The zone measurements are preferably made by scanning the plates electronically, with suitable arithmetic manipulation of the resulting video values at a plurality of selected positions for each zone.

16 Claims, 14 Drawing Figures

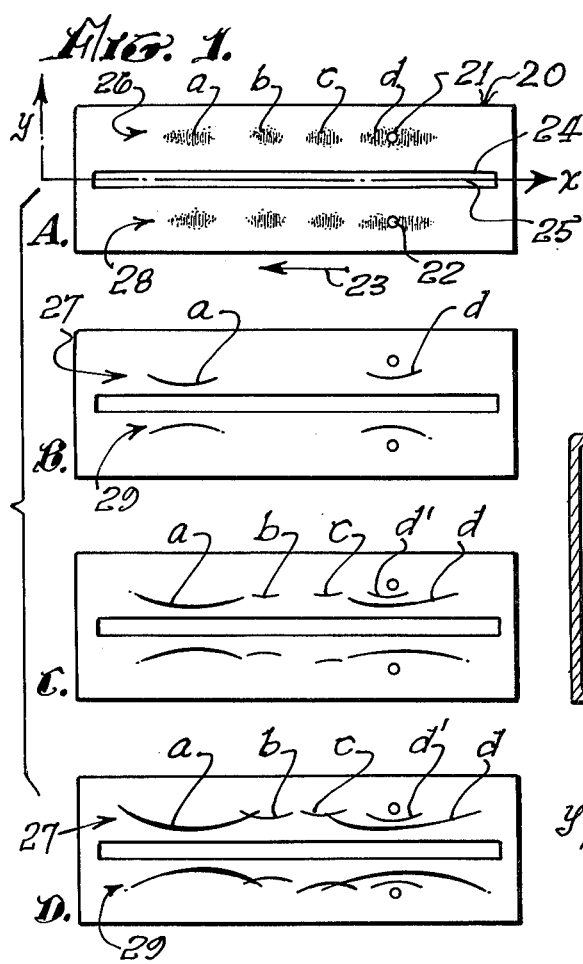
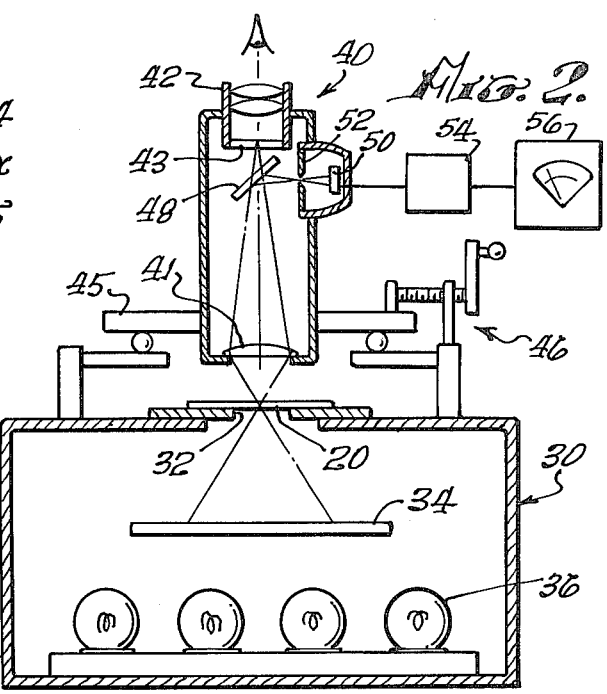
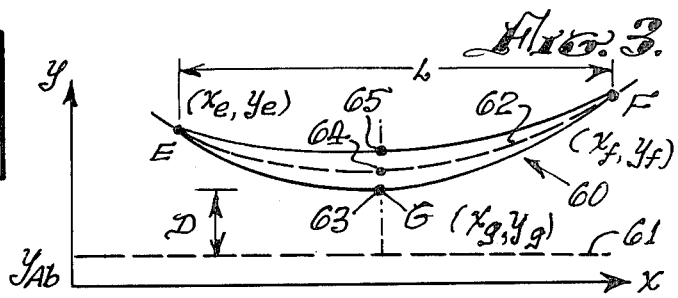
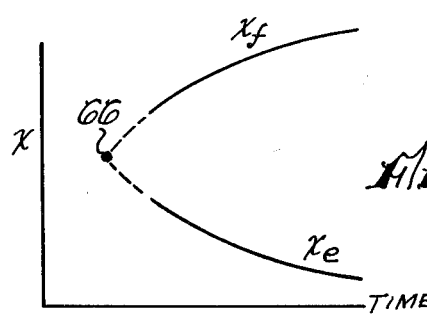
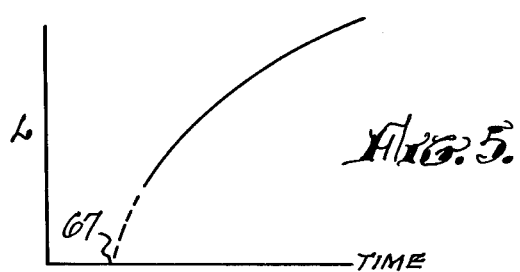
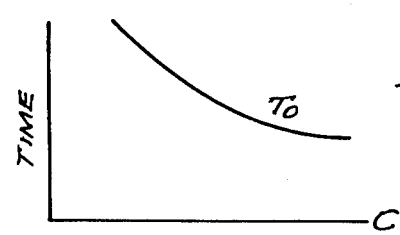
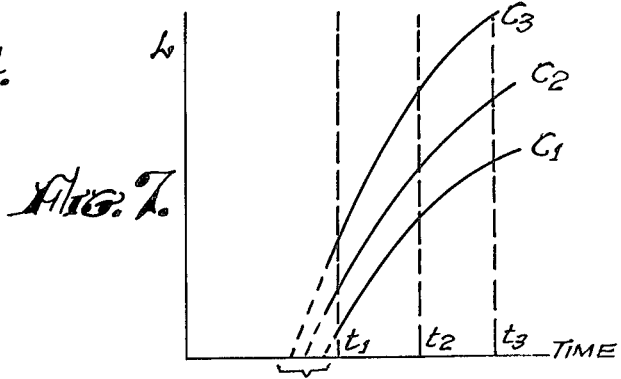
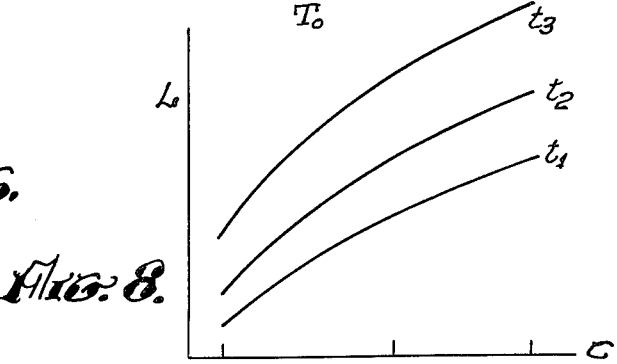

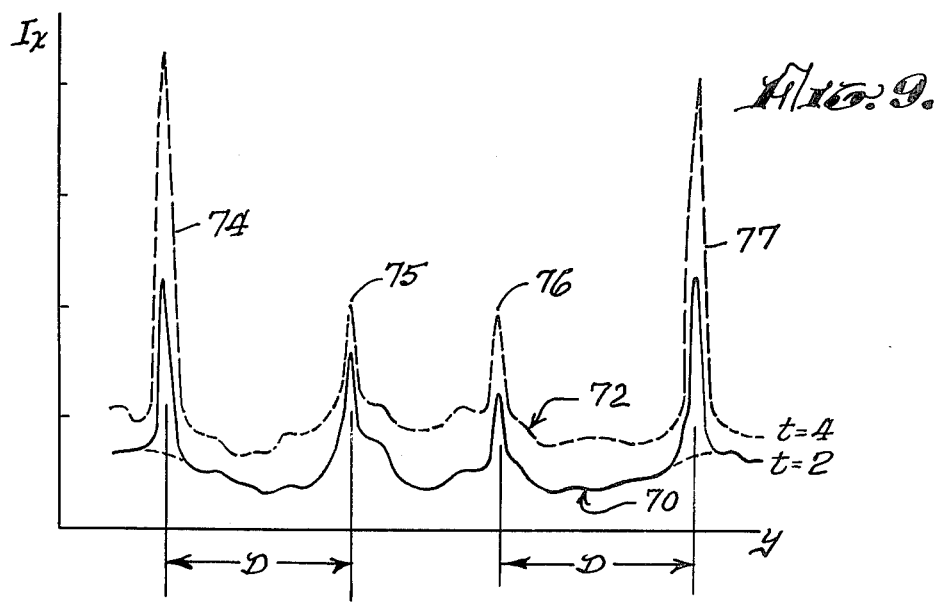
FIG. 9.
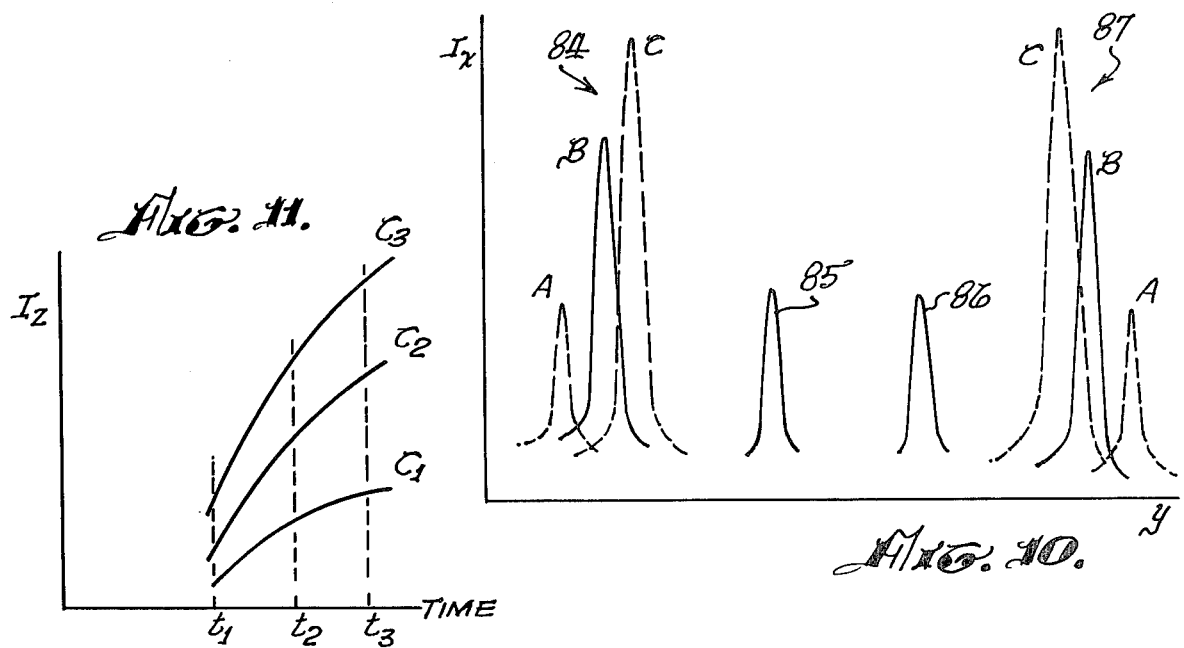
FIG. 11.
FIG. 10.
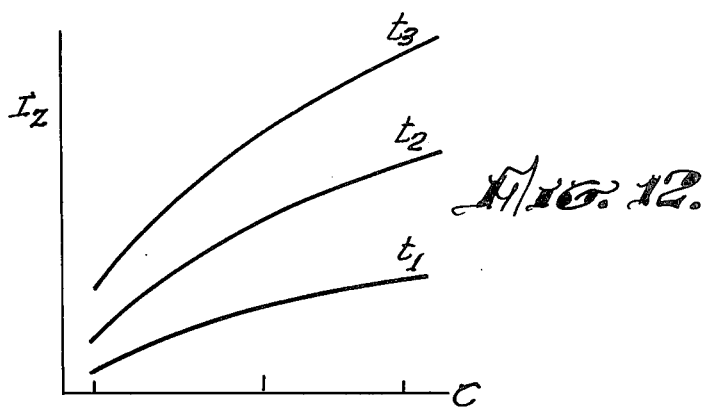
FIG. 12.

QUANTITATIVE PROTEIN ANALYSIS BY IMMUNODIFFUSION

BACKGROUND OF THE INVENTION

This invention relates generally to the quantitative measurement of proteins in mixtures, especially when only small amounts of material are available.

In view of the current rapid expansion of knowledge concerning the role of proteins in health and disease, there is an increasing need for a general, rapid and relatively economical quantitative method for protein analysis of such fluids as serum, spinal fluid, tissue extracts and the like.

The proteins occurring in such fluids are frequently identified by immunochemical procedures which depend upon precipitation of each protein by an antibody specific to the particular protein. The production of such specific antibodies is stimulated when foreign proteins (antigens) are introduced into a living body. Antisera can be prepared, containing known mixtures of such antibodies. By reacting a protein sample in vitro with such an antiserum and observing the resulting precipitation, or lack of precipitation, useful information may be obtained as to the types of proteins in the sample.

Previous attempts to obtain quantitative results with immunochemical procedures have generally employed processes which are not well suited for the present purpose. In particular, many such processes have the serious disadvantage that they require the use of antisera that are rigorously immunochemically specific for the single protein of which the concentration is to be determined. If the antiserum contains even small amounts of contaminating antibodies against other proteins that are present in the mixture, vastly erroneous results may be obtained. Although it is ordinarily possible to obtain immunochemically specific antisera which react with only a selected single protein and do not cross react with other proteins, this requires relatively complex and expensive procedures which are difficult to carry out on a routine basis and are expensive.

SUMMARY OF THE INVENTION

The present invention has successfully avoided such difficulties by employing immunochemical procedures which inherently facilitate distinction among precipitates formed by different proteins.

In preferred form of the invention, the proteins present in the initial antigen mixture are first partially fractionated by causing them to migrate in one dimension at rates that differ characteristically among the various proteins. Such migration may, for example, utilize simple diffusion, electrophoresis, or more complex techniques such as chromatography. In the illustrative case of electrophoresis, differences of electrophoretic mobility between different proteins cause the proteins to become distributed in the direction of the electrical field in accordance with their mobility. Following such initial fractionation, the resulting essentially linear distribution of proteins is brought into contact with the antiserum by relative movement in another dimension, typically by mutual diffusion in a suitable agar or agarose support medium. The precipitation zones of the respective proteins are then typically entirely separate and can be clearly distinguished. That overall process, known as immunoelectrophoresis, is well recognized as a qualitative method of great power and flexibility for detecting the presence or absence of certain antigens or the antibodies against them.

The present invention provides methods by which quantitative values for protein concentration are obtainable from measurements of the precipitation zones produced by immunoelectrophoresis, or by similar processes that may include an initial fractionation in one dimension followed by immunodiffusion in another dimension.

Useful separation of the precipitation zones of a plurality of distinct proteins is also attainable without an initial step of fractionation, if the antigen and antibody are allowed to diffuse toward each other in a manner to form elongated precipitation zones of limited length extending transversely of the primary direction of diffusion. The mobilities for diffusion of different proteins, and/or of their antibodies, are ordinarily sufficiently different that such precipitation zones are clearly distinguishable. Any overlapping that may occur is usually limited to the central portions of the zones, the zone end points being clearly separated. The quantitative procedures of the present invention are usefully applicable to immunodiffusion of the described type.

On the other hand, diffusion processes having radial or circular symmetry provide less effective resolution of a plurality of different zones, and are ordinarily useful for quantitative analysis only with antisera containing a strictly limited number of different antibodies. Such circularly symmetrical processes are of two main types. In the processes known as "radial immunodiffusion" one reactant is initially dispersed uniformly in the support medium, the second reactant diffusing radially outward in a symmetrical manner from a small circular well. The resulting precipitation zone extends from the well continuously and substantially uniformly outward to a circular outer edge. In the other main type of circularly symmetrical diffusion, one reactant is placed in a central circular well, the other in a concentric annular well, and the diffusion occurs radially between the two wells. The zones of precipitation are then typically concentric circles. That type of diffusion has been studied theoretically by one of the present applicants for the primary purpose of analyzing the precipitation process itself. See Frederick Aladjem et al, Immunochemistry, Vol. 5, pp. 217–252 (1968). Although quantitative determinations of one antigen or of one antibody can probably be made by such concentric processes, the circular zones tend to overlap, leading to ambiguity of both identification and measurement unless the number of zones is strictly limited. Accordingly, neither radial immunodiffusion nor concentric immunodiffusion is considered useful for the purposes of the present invention.

A primary object of the present invention is to obtain quantitative values for the concentration of one or more proteins in an antigen solution, utilizing immunodiffusion procedures of the above defined types, which have previously been regarded as only qualitative techniques. That has been accomplished in large part by selecting suitable parameters for measurement and computation, and by providing adequate reference standards to which the results can be compared.

In accordance with one aspect of the invention, a large number of measurements are carried out in a systematic manner as the precipitation pattern develops, and the resulting direct data are then employed for deriving values of carefully selected and relatively specific parameters of individual selected precipitation zones. Those parameter values are compared with values obtained under comparable conditions from a series of standard or reference runs which have been suitably selected and treated to facilitate reliable interpolation. That procedure has been found to yield satisfactorily consistent and reproducible quantitative values for the actual concentrations of the selected proteins in the sample.

The described collection of initial experimental data and the computations made with them can be carried out manually, if desired. They are also well adapted for semi-automatic data collection by optical and electronic scanning devices that are commercially available. Also, the necessary data processing can be made fully automatic by use of a general purpose computer of moderate capacity.

BRIEF DESCRIPTION OF THE DRAWING

A full understanding of the present invention, and of its further objects and advantages will be had from the following description of illustrative ways in which it can be carried out. The particulars of that description, and of the accompanying drawings which form a part of it, are intended only as illustration and not as a limitation upon the scope of the invention, which is defined in the appended claims.

In the drawings:

FIG. 1 is a schematic plan of an immunoelectrophoresis plate, FIG. 1A illustrating a typical distribution of proteins following electrophoresis, and FIGS. 1B, 1C and 1D illustrating successive stages of the subsequent immunoprecipitation reaction;

FIG. 2 is a schematic axial section representing typical apparatus for measuring a slide in accordance with one aspect of the invention;

FIG. 3 is a schematic drawing illustrating properties of a precipitation zone relating to the invention;

FIG. 4 is a graph representing typical dependence of zone end points upon time;

FIG. 5 is a graph representing typical dependence of zone length upon time;

FIG. 6 is a graph representing typical dependence of time of initial zone appearance upon protein concentration;

FIGS. 7 and 8 are graphs representing typical dependence of zone length upon time and upon protein concentration;

FIG. 9 is a graph showing actual intensity scans across a precipitation zone at two incubation times;

FIG. 10 is a graph representing intensity scans across precipitation zones formed by respective protein concentrations;

FIGS. 11 and 12 are graphs representing typical dependence of an intensity parameter upon time and upon protein concentration;

DESCRIPTION OF ILLUSTRATIVE EMBODIMENTS

Figure 13:
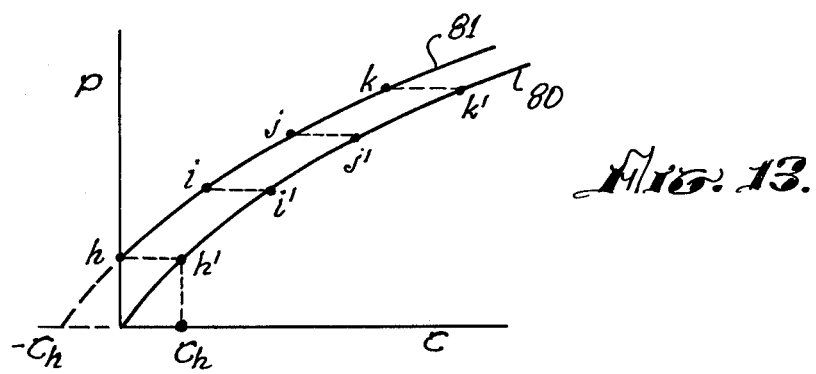
FIG. 13 is a schematic graph illustrating derivation of protein concentration values by known additions of the protein to the unknown sample.

Many aspects of the invention are well illustrated by its embodiment in the preferred process of immunoelectrophoresis, and the following description will emphasize that form of the invention, but without implying any limitation of scope.

It will be evident, for example, that if the electrophoresis of that preferred embodiment is replaced by another process which disperses the initial proteins in accordance with respective mobilities of a type other than those produced by an electric field, the nature of the precipitin zones produced by the subsequent step of immunodiffusion is not fundamentally altered. Also, if immunodiffusion is carried out directly without preliminary fractionation of the antigen sample, the resulting precipitin zones typically have many properties in common with those produced by immunoelectrophoresis. The invention is usefully embodied in such processes.

Similarly, if antigen and antibody are placed into wells for immunodiffusion, and an electric field is applied to accelerate the movement of the antigen and antibody toward each other, as in the procedure known as electroimmunodiffusion, the resulting precipitin zones retain the same basic forms as in absence of an electric field. The same is true if the immunodiffusion step of immunoelectrophoresis is aided by a suitably directed electric field. Accordingly, the term "immunodiffusion" in the present specification and claims refers to diffusion with or without an accelerating electric field.

Immunoelectrophoresis is well known as a qualitative procedure, and many forms of apparatus have been described for carrying it out, differing in detail rather than in principle. The electrophoresis and subsequent diffusion and immunoreaction are typically performed in a single layer of gel from a fraction of a millimeter to several millimeters thick carried on an optically transparent sheet. Alternatively, at an intermediate stage of the procedure, a strip or other sample of gel containing partially processed material may be cut from one layer and transferred in known manner to another carrier for subsequent processing. For the present purpose each carrier is preferably rigid and may comprise, for example, a glass microscope slide 1 inch wide and 3 inches long, or a 5 by 7 inch plate. The assembly of gel and carrier will be referred to generally as a plate, but without implying restriction either to any particular size or to rigid structure of the carrier. A preferred supporting medium is agarose saturated with barbital buffer of approximately pH 8.6 and ionic strength 0.1. Slides can be either freshly coated with gel, purchased prepared, or purchased in dehydrated form and hydrated before use. The active materials are typically inserted into wells, which may be cut from the gel coating or formed when the gel is molded on the carrier.

Each sample of antigen is typically placed in a small circular well, from which the several components of the mixture are caused to migrate selectively parallel to electrical direct current passed through the gel between conductive bridges. Following the electrophoresis, the current is discontinued and the antibody is added, typically by insertion into a trough parallel to the direction of the electrophoresis and laterally offset from the antigen well. The plates are then incubated in a moist atmosphere, typically for several hours or even days, allowing the antigens and antibodies to diffuse through the gel and form a precipitate by their characteristic reaction wherever they come together. The resulting zones of precipitation are visible by their increased scattering of light. With progressing incubation the zones change in size, form and apparent density, and may move or even disappear entirely, depending upon the rates at which additional reactants diffuse into the area of the zone of precipitation, react and form more precipitate or dissolve existing precipitate.

FIG. 1 shows schematically a plate 20 with a typical arrangement of wells, comprising the two circular antigen wells 21 and 22, spaced equally on opposite sides of the elongated antibody well or trough 24 with axis 25, which extends parallel to the direction of electrophoresis. With that geometric arrangement of wells two distinct antigen solutions, or two specimens of the same solution, can be run simultaneously against the same antibody solution on each plate. If preferred, the capacity of each plate can be multiplied, as by providing additional antibody wells outward of the two illustrated antigen wells, with additional antibody wells outward of them. Similarly, additional antigen wells may be added, spaced far enough from wells 21 and 22 in the direction of electrophoresis to prevent overlapping of the patterns. However, such increase of the capacity of each plate tends to reduce the uniformity of response of the various samples.

The shaded areas 26 and 28 in FIG. 1A represent typical approximate distributions of four varieties of protein $a$, $b$, $c$ and $d$ from duplicate samples in the respective wells 21 and 22 following a period of electrophoresis in the direction of the arrow 23. The actual protein areas, of course, do not have sharp boundaries. Since migration of the dissolved proteins is generally not visible on the plate, but becomes known only through the later formation of visible precipitate, the optimum duration of electrophoresis is determined by experience, by initial control runs, or by addition of a tracking dye. Although all proteins usually migrate in the same direction through the liquid medium, the solvent itself tends to carry a net charge and to have a resultant flow or electroosmosis relative to the gel. Hence the proteins may have a net movement in either direction relative to the well.

Following termination of electrophoresis and addition of antibody solution to well 24, precipitation zones are produced by mutual diffusion of the proteins $a$, $b$, $c$ and $d$ of FIG. 1A and the corresponding antibodies. FIGS. 1B, 1C and 1D show typical zones at respective stages of development. The absence of precipitation zones $b$ and $c$ in FIG. 1B may be due either to use of lower concentrations of antigen or antibody than was the case for zones $a$ and $d$, or to a lower diffusion coefficient of the antigens, usually a consequence of higher molecular weight, resulting in slower development of the zones of precipitation. If a particular zone does not form eventually, while either the antigen mixture or the antibody solution used is known to contain the corresponding reactant, this usually indicates that the other reactant is absent or is present only in a concentration below the limit of detection under the particular experimental conditions.

The precipitin arcs of unrelated antigens, reacting with the antibodies against them, form independently, and may cross when they are sufficiently close together, as shown in FIG. 1D; whereas the arcs of antigens that are immunochemically related typically join in a continuous reaction. The zone of precipitation $d'$ in FIGS. 1C and 1D indicates that the area $d$ of FIG. 1A actually contained two distinct proteins, illustrating the fact that even antigens which have identical electrophoretic mobility may form distinct zones of precipitation. The zones $d$ and $d'$ may alternatively be viewed as representing two distinct proteins that were initially placed in well 21 and were subjected to immunodiffusion without initial electrophoresis, the separation of the zones, and especially the clear separation of the respective zone ends, then being due to different rates of diffusion of the proteins or of their antibodies. In either case, each such zone can be analyzed independently, using any or all of the methods of analysis to be described.

Zone Measurements

In accordance with the present invention, the zones of precipitation resulting from immunoelectrophoresis are subjected to direct quantitative measurement. Such measurements may determine only the physical position on the plate of certain selected features of each precipitation zone of interest, or may include quantitative photooptical measurements of the light intensity. For both types of measurement, the time is noted and may be used as an integral part of the observational data. If the incubation process is allowed to reach equilibrium, producing a nearly static zone configuration, the exact time of measurements becomes immaterial. Measurements under such conditions may be particularly reliable.

The zones of precipitation are best viewed by placing the transparent plate on a light box arranged for dark field illumination. As typically represented in FIG. 2, plate 20 is placed over an adjustable opening 32 in the top of a light-tight box 30. A dark backing 34 of light absorbing material such as black velvet fills the field of view as seen through the mounted plate. Internal lighting 36 is arranged to illuminate the plate obliquely by reflection from the walls of the box. The plate areas that contain only gel saturated with solution appear dark, while the precipitate scatters enough light to make the zones of precipitation appear light against the darker background.

Position measurements on slide 20 can be made, for example, with the aid of a lower power microscope. As represented schematically in FIG. 2, the microscope 40 has the objective lens 41, the eye piece 42 and a set of cross hairs or other reference reticle at 43 in the focal plane. The microscope is mounted above light box 30 on a double slide mechanism 45 with screw drive 46, and with accurate scales, not explicitly shown, for reading the microscope position in two coordinates. For clarity, only one coordinate of the movement is directly indicated in the drawing. It is usually convenient to select coordinates having the $x$-axis, say, parallel to the direction of electrophoresis and to the length of the antibody well, and having the origin of coordinates at or near the well axis 25, as indicated in FIG. 1A. With the well arrangement shown, the zones on opposite sides of antigen well 24 can then be measured in the positive and the negative $y$ directions, respectively, yielding similar numerical values for both zone locations.

For measurements of the light intensity the microscope typically includes an oblique beam-splitting mirror 48 which sends part of the light to the eye piece while another part forms a real image in the plane of a disaphragm 52. A photosensitive transducer 50 of any suitable type, such as a photomulitplier or a photoemmissive device of semiconductive silicon, for example, is mounted behind diaphragm 52, which then transmits to transducer 50 only radiation from the elemental area of plate 20 that coincides optically with the cross hair image. Transducer 50 is electrically connected to a conventional amplifying circuit 54 and meter 56. The latter may be observed visually and the value recorded manually, or the meter may embody means such as analogue-to-digital circuitry and printout mechanism for automatically recording the light intensity in response to a simple command signal. It is emphasized that the apparatus of FIG. 2 is merely illustrative, and is intended to represent the wide variety of available means for performing corresponding functions.

FIG. 3 illustrates schematically certain preferred precipitation zone features which are selected by the present invention for position measurement as the zone develops. The horizonal line 61 at $y = y_{Ab}$ represents the adjacent edge of the antibody well in the immunoelctrophoresis slide. The points E and F at the coordinates ($x_e$, $y_e$) and ($x_f$, $y_f$) represent the left and right end points of the elongated zone 60. Those points are preferably on the longitudinal axis 62 of the zone, at least when their positions are located visually on the plate. Under other conditions it may be preferred to select the zone points having the largest or smallest $x$ values, regardless of the zone curvature in the $y$ direction. Whichever definition is adopted for the end points, it is, of course, adhered to throughout an entire series of related measurements.

In addition to the zone end points E and F, we have found it useful to measure coordinates of a number of intermediate points of each zone. The single point G at the coordinates ($x_g$, $y_g$) in FIG. 3 is illustrative of such points. The respective $x$ coordinates $x_g$ of such points may be selected at uniform intervals along the length of the zone. The central point of such a series may be selected midway between the zone end points or, as illustrated at G, at the point of closest approach to the antibody well. Those positions are typically different, their spacing providing a measure of the asymmetry of the zone in the $x$ direction, which depends in general upon the homogeneity of the antigen.

Since the zone has some width in the $y$ direction, the $y$ coordinate of each intermediate point such as G can be conveniently placed either at 63 at the leading edge of the zone closest to the antibody well, at 65 at the trailing edge of the zone, or at a central point 64, which is typically chosen as the point of maximum intensity. For manual observations, the most accurate determinations of concentration have been obtained when $y_g$ was placed at the leading edge 63. When an automated scanning device is used, most accurate measurements have been obtained with $y_g$ at 64. The value $y_g - y_{Ab}$ then represents the distance D between the peaks 74 and 75, say, of FIG. 9, described below.

Zone Position Parameters

As the zone develops with increasing time of incubation, the points E, F and G progressively change both their relative and their absolute positions. The primary position change is an increase in zone length. Illustrative values of $x_e$ and $x_f$ as functions of time are plotted in FIG. 4 for a typical protein concentration. Such position values may be used directly for determining protein concentration, as by comparing the values of $x_e$ and $x_f$ obtained with unknown solutions to corresponding values obtained with known concentrations of proteins at measured times. However, more reliable and accurate results are ordinarily obtainable by deriving from such initial measurements one or more functions, which will be referred to for convenience as parameters.

An important parameter of the precipitation zone employed by the present invention is the coordinate difference $x_f - x_e$, which is a measure of the length L of the precipitation zone. The variation of that parameter with time of incubation is plotted in FIG. 5 for the typical data of FIG. 4.

Another parameter that is useful for determining protein concentration in accordance with the invention is the time $T_o$ of first appearance of the zone. That time is difficult to determine by direct observation. One aspect of the invention provides a practical way of obtaining a reliable and reproducible value for the time of first appearance.

In FIGS. 4 and 5 the solid lines represent typical plots of direct experimental values. The figures also includes extrapolations of the solid curves toward earlier times. The extrapolations are shown as dashed lines. The point 66 at which the extrapolated curves of FIG. 4 meet represents a time at which the zone must have had zero length. The extrapolated curve of FIG. 5 intersects the time axis at the point 67, giving an equivalent procedure for finding $T_o$. Such extrapolation represents a reasonable and highly useful definition of the time of first appearance of the precipitation zone. That method of determining $T_o$ has the advantage that continuous observation of the plate is not required.

Position Reference Values

In accordance with the present invention, values obtained from an unknown antigen sample for a parameter, such as the zone length L or the time $T_o$ of first appearance of precipitate, are made useful for determining the concentration of a particular protein by preparing also a system of standard or reference values for that parameter. The standard values are obtained from respective antigen solutions which contain a series of different known concentrations of the protein in question, with all other conditions of the standard runs matching those of the sample run as closely as possible.

For producing such a system of standards, a series of standard antigen solutions is prepared by known laboratory method, with protein concentrations varying stepwise over the desired concentration range. Each solution is subjected to immunoelectrophoresis under rigorously controlled conditions, which thereby become standard experimental conditions for treating any unknown sample to be analyzed by reference to that standard series. The selected measurements are made, and parameters derived for each of the standard runs, and the results are recorded and typically tabulated, plotted or otherwise processed to facilitate comparison of experimental results with them.

An advantage of using the time of first appearance of the zone as a standard parameter is that standard values of $T_o$ do not involve time as a variable. That is, although the evaluation of $T_o$ by the method described above requires measurements of the zone end points at a series of definite times, once $T_o$ has been derived from those measurements the times of the respective measurements become immaterial. Thus, the values of $T_o$ can be plotted as a function of protein concentration C, yielding a single standard curve. Such a curve is represented schematically in FIG. 6, typically based on values obtained for respective concentrations by the extrapolation method described in connection with FIGS. 4 and 5. Concentration values are directly readable from the curve of FIG. 6 for an unknown sample once its $T_o$ has been measured under the defined standard conditions.

In the case of the parameter L, preparation of standard curves is less direct. Since values of the zone length L depend upon the times at which the measurements are made, the series of reference standards must be prepared in such form that they cover a range of times. FIG. 7 represents typical reference values of L, each curve obtained with an antigen solution containing a different known concentration C of the protein of interest. Each of those solutions is subjected to immuno-electrophoresis under standard conditions, and the parameter L is determined at a series of times for the respective solutions. Since in general it is not feasible to measure L for all solutions at the same moment, each measured value is initially associated with its time of measurement, and the values for the respective protein concentration are then plotted on separate curves as functions of time. A typical family of such curves for three concentrations is shown in FIG. 7. It is noted in passing that the indicated extrapolation of those curves to $L = 0$ can provide standard values of $T_o$ for plotting FIG. 6, or can provide experimental values of $T_o$ for comparison with FIG. 6.

Although the curves of FIG. 7 can be used directly as standard reference curves for the parameter L, they are not fully satisfactory because a definite concentration value for an unknown sample cannot be read directly from them. The present invention avoids that difficulty by replotting such curves as functions of concentration rather than of the time.

For that purpose vertical lines are drawn on FIG. 7 at a series of arbitrary times, shown as $t_1$, $t_2$ and $t_3$. Their intersections with the curves then provide a set of L values for different concentrations, all corresponding to the same time. Each such set of L values is replotted as a separate curve as a function of concentration. The result is an array of curves, for the respective times $t_1$, etc., each showing L as a function of protein concentration. Such an array is shown schematically in FIG. 8, and is found more convenient for comparision with an experimental parameter value than the plot against time of FIG. 7.

Position parameters other than the zone length L may be computed from measurements of the zone as it develops, including, for example, the curvature of the zone arc, the distance from the antibody well of a selected point or portion of the zone, and functions of two or more such parameters or combination with other parameters. Standard values for comparison with such values are typically obtained and treated in the manner described for the parameter L. In particular, both the $x$ and $y$ coordinate values of one or both zone end points are measured at a series of times. The resulting sets of the three variables $(x, y, t)$ are then considered to form a matrix, and are compared with standard values by conventional matrix techniques.

Light Intensity Measurements and Parameters

Turning now to the quantitative determinations of relative light intensity, it has been discovered that a single light intensity reading does not provide a useful measure of protein concentration. That is primarily due to the variability of zone shape and speed of formation, and the tendency of the intensity to change as the zone expands.

On the other hand, we have found that the variability of such factors can be largely compensated by taking a series of intensity readings at suitably selected locations and treating them collectively to evaluate an intensity parameter. A preferred procedure is to take such readings at uniform intervals along a line extending linearly across the zone of precipitation near its center, typically in the $y$ direction at a particular value of $x$. That series preferably includes several intensity values at each side of the zone area. Those offset values are then averaged to provide a measure of the background intensity, which is subtracted from each of the intensity readings within the zone. The resulting adjusted intensity values are effectively summed, yielding essentially a linear integral of the intensity along a line crossing the zone at a selected value of $x$. We have found that such a linear intensity sum $I_x$ tends to increase with incubation time in a regular and reproducible manner, the value at any given time increasing with the concentration of the reacting protein over a wide range of experiment conditions.

Typical plots of the relative intensity observed during cross-zone scans are shown in FIG. 9. The two curves were plotted by semi-automatic apparatus of the type described below, scanning in the $y$ direction at $x_g$, the point of closest approach of the precipitation zones to the antigen well. The peaks at 74 and 77 in FIG. 9 are due to the zones formed on opposite sides of an antibody well by identical protein samples in the two antigen wells of a plate similar to that of FIG. 1. The two small peaks at 75 and 76 are due to the respective edges of the antibody well, providing a convenient reference from which to measure distances such as D from selected zone points to that well. The parameter $I_x$ defined above corresponds essentially to the area under a peak such as those at 74 or 77 of FIG. 9.

Peaks 74 and 77 of FIG. 9 were made with identical samples of human serum albumin. They illustrate typical development of the precipitation zones between 2 hours of incubation (solid line curve 70) and 4 hours (dashed line curve 72). Although the zone position remains remarkably stationary during the time between those two sets of measurements, the area of each peak grows appreciably. The near identity of the peaks at 74 and 77 is noteworthy. The two curves are offset vertically by an arbitary distance for clarity of illustration.

FIG. 10 is a schematic plot illustrating typical scans in the $y$ direction on plates made with different concentrations of protein, all measured at substantially the same time of incubation. The graph brings out clearly the increasing area of the individual peaks and the shift of the entire zone toward the antibody well with increasing protein concentration progressing from peaks A to C.

Whereas the parameter $I_x$ is highly useful for determining protein concentrations, still better results are obtained from a multiple intensity parameter, obtained by summing or averaging such linear intensity sums at several different $x$ values. A typical procedure is to compute linear sums at $x_g$ and at values spaced on each side of $x_g$ by a selected interval. Averaging or summing a uniform predetermined number of such linear sums reduces experimental error and improves the overall accuracy of the determination of protein concentration.

In accordance with another, generally preferred procedure, each time the plate is scanned the number of linear sums included in the computation is increased as the length of the precipitation zone increases. An illustrative procedure of that type is to determine the linear sum of the intensity at $x_g$ and to continue to compute such sums on each side of $x_g$ until the value of the sum falls below a selected threshold. Or the process may be continued until an $x$ value is reached at which the zone is no longer clearly distinguishable from the intensity of the background. In either case, addition of all the linear sums provides a parameter which is a measure of the total intensity of the zone of precipitation at the time of the scan. In fact, that sum approximates the integral of the intensity over the area of the zone. That approximation can be obtained as precisely as is desired, within the limits of resolution of the instrumentation, by the simple expedient of reducing the $x$ and $y$ increments at which measurements are made. Accordingly, that parameter will be referred to as the total intensity parameter, and will be denoted $I_z$. The value of $I_z$ varies especially steeply as a function of protein concentration over a wide range of experimental conditions. That is because as the concentration is increased both the $x$ and $y$ dimensions of the zone increase, and the average intensity of the zone also tends to increase. That steeper dependence upon protein concentration makes the total intensity parameter especially effective as a criterion for determining the concentration.

Intensity Reference Values

After obtaining experimental values for one or more intensity parameters for an antigen sample to be analyzed, those values are compared with suitable arrays of standard values for the respective parameters, obtained under closely similar experimental conditions but with a series of protein solutions containing respective known concentrations of the protein of interest. To obtain such an array of standard values, standard runs are carried out with such standard protein solutions, and intensity measurements are made at corresponding points of the respective plates at successive times as their incubation proceeds. Standard values of the selected intensity parameter are derived from the results of those measurements, typically for each concentration and at several times. Since the procedure necessarily involves many plates, it is not generally feasible to measure the data for all concentrations at the same time. Each measured standard value of the parameter is therefor considered as a function of both concentration and time. If individual linear intensity sums $I_x$ are to be considered separately, a full indentification also requires specification of the value of $x$.

To facilitate comparison of a parameter value for an unknown sample with such an array of standard values of the parameter, all the standard values for each protein concentration are first plotted as functions of time, yielding a family of curves for respective concentrations, as represented schematically in FIG. 11. Vertical lines are then drawn on that graph at a series of selected times, each line crossing several of the concentration curves. The sets of parameter values defined by those crossings are then plotted as functions of concentration, yielding a family of curves as represented schematically in FIG. 12, each curve corresponding to a definite time of measurement. That procedure for deriving the curves of FIG. 12 from those of FIG. 11 is basically similar to the previously described procedure for handling standard values of position parameters, whereby the curves of FIG. 8 were derived from those of FIG. 7. Although it has been found more convenient to use the reference data in the form of FIGS. 8 or 12, the data as shown in FIGS. 7 and 11 can, of course, be used directly. Values of $T_o$ are obtainable by extrapolating the curves of FIG. 11 to zero intensity, in the manner described for FIG. 7.

In preparing standard reference curves for any parameter it is preferred to obtain each reference value as the average of at least three or four replicate runs. Not only is the accuracy of each value thereby increased, but a meaningful indication of the experimental error can be obtained in conventional manner, typically as the square root of the mean of the squared deviations. If the experimental error should be greater than normal in any particular case, additional runs are preferably made until the reliability of the result is brought into line.

The standard runs are preferably carried out with all conditions as nearly identical as possible to those of the experimental runs for which they are to provide reference values. In fact, a distinct set of reference values is preferably obtained for every group of experimental runs. However, for routine measurements for which the reference curve slopes are known from previous experience, even a single standard run may sometimes suffice. It is not always possible to employ identical media for preparing the experimental samples and the standard solutions. Standard antigen solutions are normally available in saline solutions of standard normality, and for many purposes such solutions can be employed directly for the required standard runs without introducing significant errors. It is ordinarily preferable, if the sample to be analyzed comprises human serum, for example, to prepare the standard solutions in a standard serum.

A further aspect of the invention provides improved accuracy, especially when the sample under study contains the protein or proteins of interest at relatively low concentrations. The standard solutions are then preferably supplemented by adding known amounts of such proteins directly to aliquot portions of the sample itself, and running the resulting solutions in parallel with the original solution, and with standards containing definitely known concentrations of the protein. Values are obtained for the desired parameter for the respective solutions all at a uniform time, using the above described technique for interpolating with respect to time if necessary. The parameter values P obtained for the regular standard solutions are plotted against protein concentration in the usual way, as indicated schematically by curve 80 in FIG. 13. Also plotted are the values of P for the original antigen sample, and for the portions of that sample to which protein was added in known amount, indicated typically as the respective points $h$, $i$, $j$ and $k$. Those points are plotted relative to the horizontal concentration axis as if the solutions contained only the protein that was added. Thus the value $h$ for the original sample is plotted at $C = 0$. Curve 81 is drawn through those points. With that illustrative arrangement of the data, the protein concentration in the original sample can be evaluated in several ways, which should theoretically give the same value. Thus, any desired number of those procedures may be used, and the resulting values averaged.

First, horizontal projection from point $h$ to intersect curve 80 at $h'$ yields the concentration value indicated at $C_h$, which corresponds to the general comparison procedure previously described. Further, similar projection of each value $i$, $j$ and $k$ to intersect curve 80 provides a measure of the concentration in terms of the lengths of the lines from $i$ to $i'$, $j$ to $j'$ and $k$ to $k'$, all of which lengths are theroetically equal. If the value of P at $h$ is somewhat uncertain, for example because the observed zone is faint, an average of all four intervals gives a more reliable value.

Another procedure has the advantage that it can not only improve the accuracy of an uncertain determination of $h$, but can also provide an answer even if the original sample contains less than the threshold value of protein needed to produce a measurable precipitation zone. In the latter case, the upper portion of curve 81 is drawn through the available points $i$, $j$ and $k$, and is extrapolated to the P axis, thus providing a determination of P at $h$. In thus projecting curve 81, standard curve 80 is a helpful guide. For example, curve 80 is shifted bodily to the left in FIG. 13 till it represents as well as possible the ponts $i$, $j$ and $k$. The intersection of the shifted curve 80 with the P axis then gives a good measure of point $h$, from which the concentration $C_h$ is found. Also, further extrapolation of curve 81 to the negative C axis at $-C_h$ gives a direct reading for the concentration, which should agree with the value $C_h$.

The described reliance upon the supplementary standard curve 81 has the great advantage of using the identical medium for the experimental and reference solutions. Especially when that medium is the human serum of a particular patient, that advantage more than overcomes any possibility of slight error in extrapolating the standard curve. By increasing the number of different amounts of added protein, the three shown illustratively in FIG. 13 being merely illustrative, and by using several runs for each amount, the reliability of the extrapolation can be increased almost without limit, and a good indication can be obtained of the experimental error that it may involve.

The usefulness of carrying out independent determinations of protein concentration of each sample with several different parameters, and of computing the experimental error for each measured value, is well illustrated by the behavior of certain abnormal proteins, such as abnormal gamma globulin, for which different parameters characteristically yield significantly different concentration values. Normal and abnormal forms of gamma globulin typically have different ranges of electrophoretic mobility, but react with the same antibody. The protein with the wider mobility range forms a longer precipitation zone, leading to higher values of the parameter L. The average intensity of the zone, as measured by a single cross scan $I_x$, for example, is therefore less than normal and the time of first appearance of the zone tends to be longer, compared to reference values produced under similar conditions by an equal initial quantity of the protein with narrower mobility range. On the other hand, the total intensity $I_z$ tends to yield approximately equal concentration values for the normal and abnormal proteins. Thus, by measuring such a protein in terms of at least two of the parameters L, $I_z$ and $T_o$, abnormally poor agreement among the values is an indication that an abnormal protein has been encountered; and that indication is greatly strengthened if the computed experimental errors show each value to be normally reliable. With that information, the values obtained can be interpreted properly, and further tests can be carried out if warranted.

Multiple Parameters

Further advantages are nearly always obtainable by employing multiple parameters which comprise specific functions of two or more parameters, such as the described position or intensity parameters. For example, the sum of the zone length L and an intensity parameter, each appropriately weighted according to its experimental error of measurement, provides a new parameter which tends to give more reliable results than either one of its components when used alone.

Another advantageous combination comprises a differential function of two parameters, one of which increases with increasing protein concentration, while the other decreases. Thus, a quotient or a difference of such parameters provides a multiple parameter with a steeper dependence upon concentration that either of its components. The time $T_o$ of first appearance of the zone is an example of a parameter having inverse relation to protein concentration, and is especially useful for constructing such quotients. The distance from the antibody well to the zone at any desired value of the $x$ coordinate, for example the distance of closest approach at $x_g$, also depends inversely upon the concentration and may be employed as a parameter in such quotients. It is generally preferred to divide the parameter with direct dependence upon concentration by that with inverse dependence, so that the resulting multiple parameter has a direct rather than inverse net dependence.

Suitable reference values for comparison to experimentally determined multiple parameters of unknown samples are typically derived from reference values obtained as already described for the respective component parameters.

Electronic Scanning of Immunoelectrophoresis Plates

Whereas the position and intensity measurements and the parameter derivations that have been described can be carried out by direct visual and manual operations, as has been indicated, an advantage of the invention is that those operations are particularly well adapted for partial or substantially complete automation.

An especially convenient and effective procedure for making the measurements required by the invention is to scan the slide with a television camera or equivalent device, which is connected to a synchronized cathode ray tube for displaying the scanned image and is provided with electronic controls of known type for extracting the video signal corresponding to a selected point of that image. The extracted video signal, representing the apparent brightness of the scanned image, is then amplified and shaped in any desired manner, and is preferably converted to digital form for visual display, conventional printout, or supply to a general purpose digital computer for further processing. Systems of that type for scanning and reproducing an image and for extracting a video signal in digital form from a selected image point are well known in the electronic art, and are available commercially in forms well adapted for the present purpose.

Figure 14:
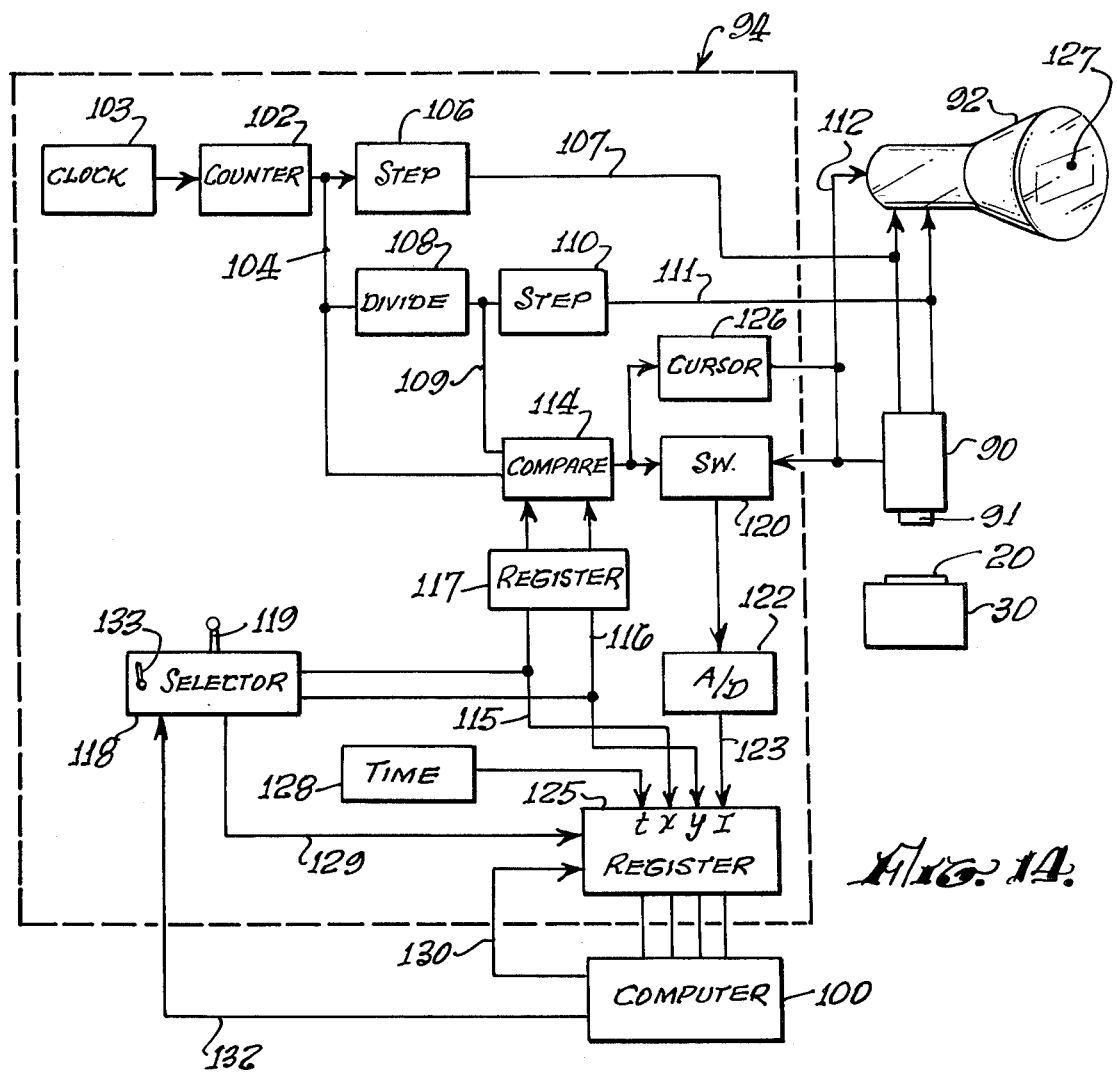
FIG. 14 is a schematic block diagram representing electronic scanning apparatus for carrying out the invention.

FIG. 14 represents schematically such apparatus, comprising the television camera 90 with lens 91 for imaging the plate 20 on the photosensitive surface of the camera, the monitor cathode ray tube 92, the scan control apparatus 94 and the general purpose computer 100. Plate 20 can be imaged at any desired magnification by conventional adjustment of lens 91. A desired portion of the plate can be centered in the field by shifting its position on its illuminated support, such as light box 30 of FIG. 2, or by conventional electronic bias controls in the camera circuits.

More particularly, the synchronized scanning movements in the television camera and monitor cathode ray tube are typically driven stepwise in both coordinates, with steps so small that the movement appears virtually continuous on the screen. The image is thereby divided into elemental areas, which can be identified, for example, by specifying their $x$ and $y$ coordinates. For manual or semi-automatic operation, the monitor display typically includes a cursor comprising an electronically produced bright spot which designates on the screen the elemental area from which the video sample is being extracted once each complete scan. The operator is provided with manually controlled electronic switching means by which he can move the cursor about on the screen under visual control. Means may also be provided for directly placing the cursor at a desired point, typically in response to $x$ and $y$ signals in digital form constituting a command address. Such signals may be derived under manual control, or supplied from a computer in response to conventional program instructions.

As illustratively shown in FIG. 14, the counter 102 counts pulses received from the clock 103, producing on the multiple lines 104 digital signals which represent successive $x$ coordinate values. Circuit 106 develops on the line 107 an analogue step voltage in response to those signals, with a step corresponding to each elemental $x$ value. The dividing circuit 108 effectively counts the beam sweeps in the $x$ direction, producing on the multiple lines 109 digital signals representing the $y$ coordinate. Circuit 110 develops on the line 111 an analogue step voltage in reponse to that count, with a step corresponding to each elemental $y$ value. The step voltages on lines 107 and 111 control the $x$ and $y$ sweep movements in camera 90 and tube 92, insuring their synchronization. The video signal from camera 90 is supplied via the line 112 to monitor tube 92, reproducing on the tube screen the brightness variations of slide 20.

The selection circuit 118 typically comprises $x$ and $y$ counters which are selectively shiftable up or down either by a single count or in a continuing series of counts in response to manual movement of the joy stick indicated schematically at 119. The resulting digital signals, representing $x$ and $y$ coordinates of a point selected for exploration, are stored in register 117. The comparison circuit 114 continuously compares the coordinates of that selected exploration address from register 117 with those of the scanning beams from lines 104 and 109. When the scanning spot reaches the stored address, typically once during each complete scan, comparison circuit 114 supplies an enabling pulse to the switching circuit 120. The video signal from camera 90 is thereby transmitted to analogue-to-digital circuit 122. The register 125 thus receives on the lines 123 a digital representation of the brightness of the scanned slide 20 at the selected exploration point. The enabling pulse from circuit 114 is supplied also to the cursor control circuit 126, superimposing upon the video signal a beam intensifying pulse which identifies that selected point on the monitor screen, as indicated schematically at 127.

Register 125 also receives the $x$ and $y$ coordinate signals from lines 115 and 116 and a digital signal continuously representing the time, developed under clock control by the time circuit 128. All of those signals are typically stored in register 125 for delivery to computer 100 in response to unload signals which may be supplied either under manual control via the line 129 from selector 118 or via the line 130 under control of the computer.

Computer 100 is preferably provided with means for independently designating an exploration address and thus obtaining input information for the spot of plate 20 that corresponds to specific requirements of any program under which it is operating. Such exploration means may comprise circuitry basically similar to selector 118, register 117 and comparison circuit 114, the selector operating in response to electronic signals which selectively indicate the required direction of movement of the exploration spot or the digital address of its required position. Rather than duplicating such apparatus, FIG. 14 indicates computer control of selector 118 by electronic signals supplied via the multiple lines 132, supplanting joy stick 119 when the switch 133 is shifted from manual position to automatic. With such control available the computer is readily programmed to carry out position and intensity measurements and parameter derivations of the general types that have been described.

For automatic scanning of plates, conventional means are provided for transferring the plates of a set in sequence from the incubation chamber to an accurately defined scanning position with suitable dark field illumination. Conventional machine-readable identification symbols are provided on each plate, as well as reference marks for insuring uniform spatial relationship between the $x$ and $y$ coordinates of the scan movements and the reagent wells on the plate. Initial scan procedure typically comprises request by the computer for video information at successive exploration addresses with a selected $x$ value and with $y$ values shifting progressively by a specified interval over the region in which zone formation is anticipated.

The video intensity values received from register 125 are stored with $x$, $y$ and $t$ data for each explored point. After each such $y$-scan, the $x$ coordinate is shifted by a specified interval and a similar $y$-scan is performed and the results recorded, until the entire area of interest has been covered. Each received intensity value is typically compared with the previously received and stored values. If the observed intensity variations exceed a set threshold characteristic of a background area, indicating presence of a precipitation zone, each intensity value within the zone is so designated in memory. Also, for each $y$-scan, the intensity maximum as the zone is crossed is identified and recorded, establishing the zone axis in terms of a series of $y$ values at uniformly spaced $x$ values. The end points of each zone are identified typically as the terminal $x$ values in each direction at which an intensity maximum was identified. If more precise location of the end points is desired, the computer is instructed to perform further scans in a defined region about each end point with reduced $x$ and $y$ intervals.

With the existing precipitation zones so located and recorded, straightforward arithmetic operations are performed on the stored data, yielding the described intensity sum parameter $I_x$ for each cross-scan of a zone in the $y$ direction; and addition of those values gives the total intensity parameter $I_z$ for the zone. Subtraction of the $x$ values at the zone ends gives the parameter L. Additional parameters may be obtained by appropriate computation as desired.

That entire scanning and computing operation for each plate typically requires at most a few seconds, so that a single time value provides adequate identification for all the resulting data. The required computer time may be further reduced by directing the computer initially to scan only limited regions of the plate where specific proteins are expected to form zones. Such preliminary scans can even be limited to a single $x$ value for each such protein; then, after a zone is found, further scans are made at adjacent $x$ values until the end points of the zone are reached.

The described measurements are preferably carried out as a unitary operation on a conplete set of plates that includes one or more unknown samples and also a set of related standard solutions of the type discussed above and sufficiently complete to permit evaluation of the unknown samples. After each scan of such a plate set, the computer is preferably directed to carry out interpolations equivalent to the graphical procedure described above for obtaining one or more values for the concentration in the sample of each of the proteins for which precipitation zones were found. If, as is preferred, the standard runs include several identical examples of each standard protein solution and/or of each test sample, the available data permit evaluation also of the probable experimental error for each calculated concentration value. Computer routines for such calculations are well known. Several independent determinations are preferably made of the concentration of each protein in the sample, typically by reference to respective parameters; an average is then computed, with each value weighted in the usual way according to its probable error.

If the computed probable error for that average is within the specified range for the particular sample under study, no further measurements are needed. The computer then produces a conventional printout or other record of the final results, together with as much of the original data as may be requested by the program. For example, the physician for whom the analysis is being carried out may require a complete copy of all the data on magnetic tape or the like for possible future reference. Also, photographs of the immunodiffusion plate can be taken using the monitor tube.

Ordinarily, the first scan does not permit an adequate quantitative determination of all, or even one, of the proteins of interest. The plates are then typically returned to the incubation chamber for a set time interval. Since the diffusion time increases very rapidly with the diffusion distance, the time required for zone formation by immunodiffusion increases rapidly with the scale of the plates, or, more particularly, with the spacing of the path of electrophoresis from the antibody well. When the immunoelectrophoresis is carried out on microscope slides the zone development after a few hours of incubation may correspond to many hours of immunodiffusion on larger plates. Although the latter tend to give the more reliable results for a single sample, time is not always available. Moreover, when the smaller plates are processed with automated measurements the accuracy can be greatly increased by multiple determinations.

After a suitable length of supplementary incubation, which may vary from a few minutes, say, to an hour or more, the above described scanning process is repeated, typically for the entire set of test plates and the corresponding standards. The computer is typically instructed to explore plate areas where zones were expected but not found during the previous scan; and also areas corresponding to the previously found and recorded precipitation zones, preferably allowing for specified expansion or movement of those zones which are set into the program on the basis of previous experience. Thus, the computer operations can maintain a continuity of treatment of the respective protein zones between one scan and the next.

All of the measurements are preferably updated during each scan, leading typically to new determinations of the concentration of each protein in the sample. The new data values can replace the old in the computer memory, or can be stored as a unit supplementing the previous set or sets of values. The former procedure is more economical of memory capability, while the latter permits more detailed and flexible comparison among the different sets of data. If all expected zones are found, and all protein concentration values have probable errors within the specified criterion, that portion of the experiment is terminated. Otherwise, the plates are given a further period of incubation, followed by another similar measurement procedure.

Such repeated measurements may be continued as long as desired, especially since the data tend to become progressively more consistent as the zones mature. As a practical matter, however, it is preferred to include in the program some limit, after which the results obtained are printed out as already indicated, no further scans being made. Rather than defining a sharp cutoff, the computer may be instructed, after a set number of measurement cycles, to relax progressively the required precision of the result.

Occasionally two precipitation zones due to distinct proteins are so close together that their normal growth ultimately produces overlap. For zones produced by immunoelectrophoresis, such overlap normally occurs at or near the zone ends, leading to crossing of the zones as shown typically for zones a and b of FIG. 1D. When immunodiffusion is carried out without initial fractionation, the overlap tends to be confined to the zone center portions, as when zones $d$ and $d'$ of that figure grow together. The computer is typically programmed to anticipate such a zone overlap, to recognize it when it has occurred, and then to make suitable modification in the procedure used for deriving the various parameters.

When the proteins under study are such that overlaps are anticipated, the initial scan of each plate is preferably made at an early stage of zone development, such as that of FIG. 1B, before zone overlaps have occurred. The zone axis and end points can then be located without ambiguity. The computer is typically programmed as part of the regular processing of each scan to check for actual overlaps, for example by comparing the $(x,y)$ coordinates for each measured point of a zone axis with those for the adjacent zones, coincidence within a specified threshold indicating an overlap. All scans preferably also include a check for potential overlaps. For example, the computer extrapolates each zone axis beyond the observed end points and compares the extrapolated axis points of adjacent zones. Such axis extrapolation may comprise a simple linear extension in the direction of the axis slope computed from the last few points of the axis at each end. Alternatively, the entire observed zone axis may be fitted by an analytical curve of second order, such as a parabola or hyperbola, using a conventional least squares routine. Extrapolated points can then be directly computed from the equation for that curve.

When an actual overlap is found on one half of a zone, sufficiently accurate compensation can often be made by simply replacing the observed intensity values in the area of overlap with the values observed at the corresponding points of the other half of the zone. Such correspondence between two points for zones due to immunoelectrophoresis is typically defined as equal $x$ spacing on opposite sides of $x_g$ of the point of closest approach to the antibody well; and for zones due to direct immunodiffusion is defined as equal $y$ spacing on opposite sides of the zone axis. The axis within the area of overlap can usually be located by extrapolation.

More elaborate and accurate compensation procedures are also available, if desired. For example, the computer is instructed to select the symmetrically placed point of the unaffected half of the zone, as just described, and adjust the intensity or other value measured at that point to take account of any actual lack of symmetry of the zone, due to a difference of shape, intrinsic intensity or the like. That unsymmetry can be determined, for example, by comparing the values that were obtained for the two points during a previous scan prior to the overlap, and applying the ratio of those values as a correction factor for the current value at the selected point.

A further illustrative compensation procedure takes account also of the intensity value actually measured at the region of overlap, which is due, of course, partly to one zone and partly to the other. The computer is instructed to divide that observed value at each point of overlap in an appropriate ratio. A suitable approximate ratio may be obtained by comparing measured values for the two zones at the respective symmetrically placed points already described, either with or without the described adjustment of those values.

Whenever possible, it is preferred to employ two or more distinct computation procedures for compensating for areas of overlap, averaging the results and determining the probable error. Selection of an appropriate routine will in general depend upon the degree of precision required in the final determination of protein concentration. It is emphasized, however, that the region of overlap is ordinarily a small fraction of the entire area of a zone. Hence even quite appreciable errors in approximating the true zone intensity at each point of such a region still do not affect the final result significantly.

Also, for each of the described types of overlap, it is usually possible to make the determination of protein concentration in terms of parameters that are defined by portions of the zone not affected by the overlap. Thus, the measurements preferably employed are those near the zone center for processes similar to immunoelectrophoresis, and those near the zone ends for processes similar to direct immunodiffusion.

It will be recognized by those skilled in the art that many particulars of the described procedures can be replaced by their obvious equivalents without departing from the proper scope of the present invention. For example, values for those parameters that do not require a series of measurements at successive incubation times can be obtained from measurements made after the incubation process has been allowed to reach substantial equilibrium. Such measurements have the advantage that the zone configurations are virtually static, and the exact time of measurement is therefore not crucial. As a further example, at any desired stage of the incubation the zones of precipitation can be stained in known manner with an appropriate dye, and zone measurements can then be made using selectively transmitted light. That method of measurement is usually most useful after equilibrium has been reached, since it is then not necessary to assign a precise time of measurement.

In summary, methods have been described by which immunodiffusion, immunoelectrophoresis and analagous processes can be used to provide truly quantitative measurement of the concentrations of individual proteins in biological fluids. Actual use of the described methods has demonstrated that protein concentrations can be determined within five percent or better. The invention thus provides an effective and convenient method for making a wide variety of experimental and diagnostic determinations.

We claim:

1. Method of obtaining a quantitative measurement of the concentration of a protein in an antigen sample which has been subjected to immunoelectrophoresis including the steps of producing selective protein migration by electrophoresis in one dimension in a thin layer of supporting medium, and subjecting the antigen sample after said migration to immunodiffusion with an antibody source containing an antibody specific to said protein, the protein and antibody diffusing into reactive contact in another dimension through an area of said medium layer intially free of both antigen and antibody and reacting to form an elongated precipitation zone; said method comprising scanning the zone by optical means under dark field illumination, at a selected time following initiation of said diffusion, along a plurality of generally parallel mutually spaced scan paths which cross the zone transversely to develop electrical intensity signals representing the intensity of the scattered light at a series of positions on each scan path, said positions being distributed partly within the zone and partly outside the zone, deriving from said intensity signals for a plurality of said positions within the zone an electrical sum signal representing the sum of the effective excess of each of the intensities within the zone over intensities outside the zone, and comparing the resulting sum signal with a set of reference sum signals derived from corresponding measurements of reference zones produced by equivalent immunoelectrophoresis of a plurality of reference antigen solutions containing respective known concentrations of said protein, thereby providing a quantitative measure of the concentration of said protein.

2. Method according to claim 1 wherein said step of scanning the zone to develop electrical intensity signals is repeated at a series of definite times as the individual zone develops, and the steps of deriving and comparing sum signals are carried out for each of said times, using corresponding respective development times of said reference zones.

3. Method according to claim 2 including extrapolating said electrical sum signals back in time to zero value to determine a time of initial appearance of the zone, and comparing the resulting value of the time of initial appearance of the zone with a set of reference values derived by similar extrapolation to zero of corresponding reference sum signals representing a similar series of definite times, thereby providing a further quantitative measure of the concentration of said protein.

4. Method according to claim 1 wherein said step of scanning the zone to develop electrical intensity signals is carried out after said immunodiffusion has reached substantial equilibrium.

5. Method according to claim 1 wherein said step of scanning the zone to develop electrical signals comprises forming an optical image of the zone at the image surface of a video camera tube, representing the intensity of the image at each said position as a digital representation, and storing in a memory associated with a digital computer the digital representations and digital addresses identifying the respective image positions.

6. Method according to claim 1 wherein said scan paths include at least one path spaced beyond each end of the zone, and said method includes deriving electronically as a measure of the length of the zone an electronic signal representing the separation of the two outermost scan paths that include at least one said position within the zone for which said intensity signal has a distinct excess over intensity signals at positions outside the zone, and comparing the resulting zone length signal with the set of reference zone length signals derived correspondingly from said reference zones, thereby providing a further quantitative measure of the concentration of said protein.

7. Method according to claim 6 wherein a plurality of equivalent antigen samples and a plurality of equivalent samples of each said reference solutions are subjected to said immunoelectrophoresis and to said subsequent steps of measurement and analysis, said method including the steps of electronically computing the respective probable experimental errors of said quantitative measures of the concentration of said protein obtained from said sum signals and obtained from said zone length signals, and electronically comparing the difference of said quantitative measures with a summation of said experimental errors to detect presence of an abnormal condition of said protein.

8. Method according to claim 1 wherein said positions at which light intensity signals are developed include at least one position in said zone on one side thereof and in a region of overlaps with another zone, and said step of scanning the zone to develop intensity signals includes developing an electrical intensity signal at a second position which is correspondingly placed on the other side of the first said zone and in a region free of overlap, and employing the so developed intensity signal as the zone intensity signal for said one position.

9. Method according to claim 1 wherein said positions at which intensity signals are developed include at least one position which is in said zone on one side thereof and is in a region of overlap with one side of another zone, and said step of scanning the zone to develop intensity signals includes developing an electrical intensity signal at a second position which is correspondingly placed on the other side of the first said zone and in a region free of overlap, developing a further electrical intensity signal at a third position which is correspondingly placed on the other side of said other zone and in a position free of overlap, and utilzing as the zone intensity signal for said one position a value derived electronically from the intensity signal developed thereat and the ratio of the intensity signals developed at said second and third positions.

10. Method according to claim 1 wherein the positions represented in said sum signal include a plurality of positions on each of said scan paths.

11. Method according to claim 1 wherein the positions represented in said sum signal are all on one scan path, said method including deriving sum signals for each said scan path and comparing such individual sum signals with corresponding sets of reference sum signals.

12. Method according to claim 1 wherein said scan paths include at least one path spaced beyond each end of the zone, and said step of scanning the zone to develop electrical intensity signals is repeated at a series of definite times as the individual zone develops, and said method includes deriving electronically for each of said times, as a measure of the length of the zone, an electronic signal representing the separation of the two outermost scan paths that include at least one said position within the zone for which said intensity signal has a distinct excess over intensity signals at positions outside the zone, extrapolating said zone length signals back in time to zero value to determine a time of initial appearance of the zone, and comparing the resulting time of initial appearance of the zone with a set of reference values derived by similar extrapolation to zero of corresponding zone length signals representing respective known concentrations of said protein, thereby providing a further quantitative measure of the concentration of said protein.

13. Method according to claim 1 including the steps of deriving electronically from said electrical intensity signals a further quantitative measure of the concentration of said protein, which measure differs characteristically from the first said quantitative measure in presence of certain abnormalities of said protein, and comparing the first said quantitative measure and said further quantitative measure to detect presence of such abnormality.

14. Method of obtaining a quantitative measure of the concentration of a protein in an antigen sample which has been subjected to immunoelectrophoresis, said method comprising scanning the zone by optical means under dark field illumination at a selected time following initiation of said diffusion to develop a plurality of electrical intensity signals representing the intensity of the scattered light at respective positions which form a two-dimensional array distributed partly within the zone and partly outside the zone, deriving electronically from said intensity signals a plurality of electrical parameter signals representing respective zone parameters, said parameters including at least one parameter exhibiting substantially uniform values for normal and abnormal protein fractions and at least one other parameter exhibiting characteristically different values for normal and abnormal protein fractions, comparing the parameter signal for at least said one parameter with a set of reference parameter signals derived from corresponding measurements of reference zones produced by equivalent immunoelectrophoresis of a plurality of reference antigen solutions containing respective known concentrations of said protein to provide a quantitative measure of the concentration of said protein in said sample, and electronically analyzing the relative values of said parameter signals for a plurality of said parameters including said other parameter to detect presence of an abnormal protein fraction.

15. Method according to claim 14 wherein said one parameter comprises a summation of intensity signals for positions distributed substantially uniformly in said zone, and said other parameter comprises the length of said zone.

16. Method according to claim 14 wherein said one parameter comprises a summation of intensity signals for positions distributed substantially uniformly in said zone, and said other parameter comprises the time of initial appearance of said zone.

* * * * *